United States Patent [19]

Kato et al.

[11] Patent Number: 6,033,867
[45] Date of Patent: Mar. 7, 2000

[54] FRUCTOSYL AMINO ACID OXIDASE, PROCESS FOR PRODUCING THE SAME, AND METHOD OF ASSAYING AMADORI COMPOUNDS USING THE ENZYME

[75] Inventors: Nobuo Kato, Kyoto; Yasuyoshi Sakai, Shiga; Yoshiki Tani, Kyoto; Hiroshi Fukuya, Kyoto; Masayuki Yagi, Kyoto; Toshikatsu Sakai, Kyoto; Kaori Ishimaru, Kyoto; Satoshi Cyousa, Kyoto, all of Japan

[73] Assignee: Kyoto Daiichi Kagaku Co., Ltd., Kyoto, Japan

[21] Appl. No.: 09/077,523

[22] PCT Filed: Dec. 2, 1996

[86] PCT No.: PCT/JP96/03515

§ 371 Date: May 29, 1998

§ 102(e) Date: May 29, 1989

[87] PCT Pub. No.: WO97/20039

PCT Pub. Date: Jun. 5, 1997

[30] Foreign Application Priority Data

Nov. 30, 1995 [JP] Japan ................... 7-312342
Jul. 22, 1996 [JP] Japan ................... 8-192003

[51] Int. Cl.[7] .............. C12Q 1/26; C12N 9/04; C12N 9/62; C12N 1/14
[52] U.S. Cl. .............. 435/25; 435/29; 435/190; 435/225; 435/256.1
[58] Field of Search .............. 435/25, 189, 190, 435/191, 256.1, 913, 29, 225

[56] References Cited

U.S. PATENT DOCUMENTS 4,985,360   1/1991   Takahashi et al. ............ 435/189
5,370,990  12/1994   Staniford et al. ............ 435/4
5,712,138   1/1998   Kato et al. ............ 435/189
5,789,221   8/1998   Kato et al. ............ 435/190

FOREIGN PATENT DOCUMENTS 5-192193   8/1986   Japan ............ C12Q 1/37
3-155780   7/1991   Japan ............ C12N 9/06
 4-4874    1/1992   Japan ............ C12N 9/06

OTHER PUBLICATIONS

Horiuchi et al. Purification and properties of fructosylamine oxidase from Aspergillus sp. 1005 Agric. Biol. Chem. 55(2), pp. 333–338 (Feb. 1991).

Yoshida et al. Distribution and properties of fructosyl amino acid oxidase in fungi. Appl. Environ. Microbiol. 61 (12), pp. 4487–4489. (1995).

Yoshida et al. Primary structures of fungal fructosyl amino acid oxidases and their application to the measurement of glycated proteins. EurJ. Biochem. 242 (3), pp. 499–505. (Dec. 15, 1996).

*Primary Examiner*—Ralph Gitomer
*Assistant Examiner*—Marjorie A. Moran
*Attorney, Agent, or Firm*—Birch, Stewart, Kolasch & Birch, LLP

[57] ABSTRACT

The present invention relates to a fructosyl amino acid oxidase that is obtainable from a culture of a strain of the genus Aspergillus. This strain grows in a selective medium containing at least either of fructosyl lysine and fructosyl-$N^{\alpha}$-Z-lysine and is capable of producing a fructosyl amino acid oxidase.

5 Claims, 8 Drawing Sheets

STABILITY OF FAOD-A AGAINST TEMPERATURE

FRUCTOSYL AMINO ACID OXIDASE, PROCESS FOR PRODUCING THE SAME, AND METHOD OF ASSAYING AMADORI COMPOUNDS USING THE ENZYME

This application claims the benefit under 35 U.S.C. §371 of prior PCT International Application No. PCT/JP96/03515 which has an International filing date of Dec. 2, 1996 which designated the United States of America, the entire contents of which are hereby incorporated by references.

TECHNICAL FIELD

The present invention relates to a novel fructosyl amino acid oxidase. More particularly, it relates to a process for producing a fructosyl amino acid oxidase from the genus Aspergillus, a method of assaying an amadori compound using the enzyme, and a reagent or a kit containing the enzyme.

BACKGROUND ART

When reactive substances such as proteins, peptides and amino acids having an amino group(s) coexist with a reducing sugar such as aldose having an aldehyde group(s), they combine non-enzymatically and irreversibly through the amino and aldehyde groups, which is followed by the amadori rearrangement to form an amadori compound. The production rate of an amadori compound being a function of the concentration of reactants, contacting period, temperature, and the like, various useful information about a sample containing such a reactive substance(s) can be derived from the amount of amadori compounds. Examples of materials containing an amadori compound include food products such as soy sauce and body fluids such as blood.

In a living body, fructosylamines are formed through the glycation reaction between glucose and various amino acids. For example, fructosylamines produced when hemoglobin and albumin in blood are glycated are called glycohemoglobin and glycoalbumin, respectively. The reducing ability of glycated derivative of a protein in blood is called "fructosamine". The concentration of these glycated derivatives in blood reflects an average level of blood sugar over a given period of time, and the determination thereof can be a significant index for diagnosis and control of conditions of diabetes. Therefore, the establishment of a method of measuring an amadori compound in blood must be clinically very useful. Further, the state of preservation and period after production of a food product can be estimated on the basis of the amount of amadori compounds in the food product, and, therefore, the method of measuring an amadori compound also contributes to the quality control of a food product. As mentioned above, an assay of amadori compounds should be useful in a wide range of fields involving medicine and food products.

Examples of assays of amadori compounds include a method which utilizes high performance liquid chromatography [Chromatogr. Sci. 10: 659 (1979)], a column filled with solid materials to which boric acid is attached [Clin. Chem. 28: 2088–2094 (1982)], electrophoresis [Clin. Chem. 26: 1598–1602 (1980)] or antigen-antibody reaction [JJCLA 18: 620 (1993), J. Clin. Lab. Inst. Reag. 16: 33–37 (1993)], a method for measuring the fructosamine [Clin. Chim. Acta 127: 87–95 (1982)], a calorimetric determination following the oxidization with thiobarbituric acid [Clin. Chim. Acta 112: 197–204 (1981)], or the like. These existing methods, however, require an expensive device(s) and are not necessarily accurate and rapid enough.

In the field of clinical assay and food analysis, a method utilizing enzymatic process has become more and more popular, which makes it possible to analyze an intended substance selectively with accuracy and rapidity owing to characteristics of enzymes (specificity in terms of substrate, reaction, structure, active site, etc.)

There have been provided assays for determining amadori compounds on the basis of the amount of oxygen consumed or hydrogen peroxide generated in the reaction between an amadori compound and an oxidoreductase (e.g. Japanese Patent Publication (KOKOKU) Nos. 5-33997 and 6-65300, and Japanese Patent Publication (KOKAI) Nos. 2-195900, 3-155780, 4-4874, 5-192193 and 6-46846). Further, assays of glycated protein for the diagnosis of diabetes have also been proposed (Japanese Patent Publication (KOKAI) Nos. 2-195899, 2-195900, 5-192193 (EP-A-0526150), 6-46846 (EP-A-0576838).

The reaction between an amadori compound and an oxidoreductase can be represented by the following general formula:

$$R^1-CO-CH_2-NH-R^2+O_2+H_2O \rightarrow R^1-CO-CHO+R^2-NH_2+H_2O_2$$

wherein $R^1$ is an aldose residue and $R^2$ is an amino acid, protein or peptide residue.

Examples of enzymes which catalyze the above reaction are as follows:

1. Fructosyl amino acid oxidase derived from Corynebacterium (Japanese Patent Publication (KOKOKU) Nos. 5-33997 and 6-65300) or Aspergillus (Japanese Patent Publication (KOKAI) No. 3-155780)];
2. Fructosylamine deglycase derived from Candida (Japanese Patent Publication (KOKAI) No. 6-46846);
3. Fructosyl amino acid deglycase derived from Penicillium (Japanese Patent Publication (KOKAI) No. 4-4874);
4. Ketoamine oxidase derived from Corynebacterium, Fusarium, Acremonium or Debaryomyces (Japanese Patent Publication (KOKAI) No. 5-192193)]; and
5. Alkyllysinase which can be prepared according to the method described in J. Biol. Chem., Vol. 239, pp. 3790–3796 (1964).

Assays involving these existing enzymes, however, have drawbacks. For instance, indexes for the diagnosis of diabetes in blood are glycated albumin, glycated hemoglobin and fructosylamine. Glycated albumin is formed when glucose is bound to a lysine residue at its e-position in a protein [J. Biol. Chem., 261: 13542–13545 (1986)]. In the case of glycated hemoglobin, glucose is also bound to the N-terminal valine residue of β-chain in addition to a lysine residue [J. Biol. Chem. 254: 3892–3898 (1979)]. Therefore, it is necessary to use an enzyme more specific for fructosyl lysine compared to fructosyl valine in the determination of glycated proteins as an index of diabetes. However, an enzyme derived from Corynebacterium does not act on fructosyl lysine. The enzyme from Aspergillus disclosed in Japanese Patent Publication (KOKAI) No. 3-155780 is less active on fructosyl lysine than fructosyl valine and is not known about the action on glycated proteins or hydrolyzed products thereof. The ketoamine oxidase described in Japanese Patent Publication (KOKAI) No. 5-192193 can act on fructosyl valine, but does not afford an accurate assay of glycated proteins comprising a lysine residue bound to a sugar. Because the fructosylamine deglycase is highly specific for di-fructosyl lysine, it is inadequate for determining specifically a substance in which a lysine residue is glycated at the ε-position and/or a valine residue is glycated. Furthermore, a method using an alkyllysinase would be unreliable or inaccurate because the said enzyme is non-specific and reacts with substances comprising a lysine residue associated with a non-sugar moiety. The enzyme from Penicillium (Japanese Patent Publication (KOKAI) No. 4-4874) reacts on both of fructosyl lysine and fructosyl alanine.

As described above, the existing enzymes cannot necessarily give an accurate assay of intended glycated proteins and therefore the development of an enzyme more specific for fructosyl lysine compared to fructosyl valine has been demanded.

In general, for the improvement of accuracy and usefulness of an assay involving an enzymatic process, it is essential to use an enzyme having a catalytic activity suitable for the purposes of a given assay. Thus, it is necessary to select an appropriate enzyme taking many factors such as the substance (i.e., substrate) to be determined, the condition of the sample, measuring conditions, and the like, into consideration in order to carry out the assay with accuracy and reproducibility. To select such an enzyme, it is required that many enzymes are provided and characterized in advance.

DISCLOSURE OF INVENTION

The present inventors have intensively studied for purposes of providing a novel fructosyl amino acid oxidase specific for amadori compounds, especially, glycated proteins, and have found that a strain of the genus Aspergillus, when cultured in the presence of fructosyl lysine and/or fructosyl $N^\alpha$-Z-lysine, produces an enzyme with the aimed activity.

Thus, the present invention provides a fructosyl amino acid oxidase that is obtainable from a culture of a strain of the genus Aspergillus, which strain selectively grows in a selective medium containing at least either of fructosyl lysine and fructosyl-$N^\alpha$-Z-lysine and is capable of producing a fructosyl amino acid oxidase.

A medium containing fructosyl lysine or fructosyl $N^\alpha$-Z-lysine, which is used for culturing a microorganism producing fructosyl amino acid oxidase, contains fructosyl lysine and/or fructosyl $N^\alpha$-Z-lysine (hereinafter, may be abbreviated as "FZL") obtained by autoclaving glucose together with lysine and/or $N^\alpha$-Z-lysine at 100 to 150° C. for 3 to 60 minutes.

As described below, the fructosyl amino acid oxidase of the present invention is specific for the both of fructosyl lysine and fructosyl valine, and is characterized in that the activity on individual substrate is almost the same or higher in connection with fructosyl lysine. Throughout the specification, the fructosyl amino acid oxidase originated from the genus Aspergillus of the present invention may be referred to as "FAOD", "FAOD-A" or "FAOD-L".

BEST MODE FOR CARRING OUT THE INVENTION

The enzyme of the present invention can be prepared by culturing a strain of the genus Aspergillus capable of producing an FAOD in a medium containing fructosyl lysine and/or FZL. Examples of such a strain includes *Aspergillus terreus* (IFO 6365, FERM BP-5756), *Aspergillus terreus* GP1 (FERM BP-5684), *Aspergillus oryzae* (IFO 4242, FERM BP-5757), and *Aspergillus oryzae* (IFO 5710).

Fructosyl lysine and/or FZL used for the preparation of an FAOD of the present invention can be prepared by autoclaving 0.01 to 50% (w/w) glucose together with 0.01 to 20% (w/w) lysine and/or $N^\alpha$-Z-lysine in a solution at 100 to 150° C. for 3 to 60 minutes. Specifically, it is prepared by autoclaving a solution containing, in a total volume of 1000 ml, 200 g of glucose and 10 g of $N_{60}$-Z-lysine at 120° C. for 20 minutes.

A medium containing fructosyl lysine and/or FZL (hereinafter, referred to as FZL medium) is obtainable by adding fructosyl lysine and/or FZL obtained in a manner described above to any one of conventional media, but it can be conveniently prepared by autoclaving a mixture (preferably, pH 5.5 to 6.0) comprising 0.01 to 50% (w/w) glucose, 0.01 to 20% (w/w) lysine and/or $N^\alpha$-Z-lysine, 0.1% (w/w) $K_2HPO_4$, 0.1% (w/w) $NaH_2PO_4$, 0.05% (w/w) $MgSO_4 \cdot 7H_2O$, 0.01% (w/w) $CaCl_2 \cdot 2H_2O$ and 0.2% (w/w) yeast extract at 100 to 150° C. for 3 to 60 minutes.

The medium usable for the production of an FAOD of the present invention can be a synthetic or natural medium which is generally used in the art and contain a carbon source, nitrogen source, inorganic substance and other nutrients. Examples of carbon source include glucose, xylose, glycerin, and the like; examples of nitrogen source include peptone, casein digest, yeast extract, and the like; and examples of inorganic substance include sodium, potassium, calcium, manganese, magnesium, cobalt, and the like, which are usually contained in a normal medium.

The FAOD of the present invention can be induced to the highest extent when a microorganism capable of producing the same is cultured in a medium containing fructosyl lysine and/or FZL. Examples of preferred medium include an FZL medium (e.g., 1.0% glucose, 0.5% FZL, 1.0% $K_2HPO_4$, 0.1% $NaH_2PO_4$, 0.05% $MgSO_4.7H_2O$, 0.01% $CaCl_2.2H_2O$ and 0.01% vitamin mixture), in which FZL is used as the sole nitrogen source and glucose as the carbon source. A medium (pH 5.5 to 6.0) containing 20 g (2%) of glucose, 10 g (1%) of FZL, 1.0 g (0.1%) of $K_2HPO_4$, 1.0 g (0.1%) of $NaH_2PO_4$, 0.5 g (0.05%) of $MgSO_4.7H_2O$, 0.1 g (0.01%) of $CaCl_2.2H_2O$ and 2.0 g (0.2%) of yeast extract in 1,000 ml of a total volume is especially preferred. An FZL medium can be prepared by adding FZL to any of conventional medium, or by autoclaving a medium containing glucose together with $N^\alpha$-Z-lysine. The medium obtained by either method is colored brown owing to the presence of fructosyl lysine and/or FZL and is therefore referred to as "FZL brown-colored medium or GL (glycated lysine and/or glycated $N^\alpha$-Z-lysine) brown-colored medium".

Figure 1:
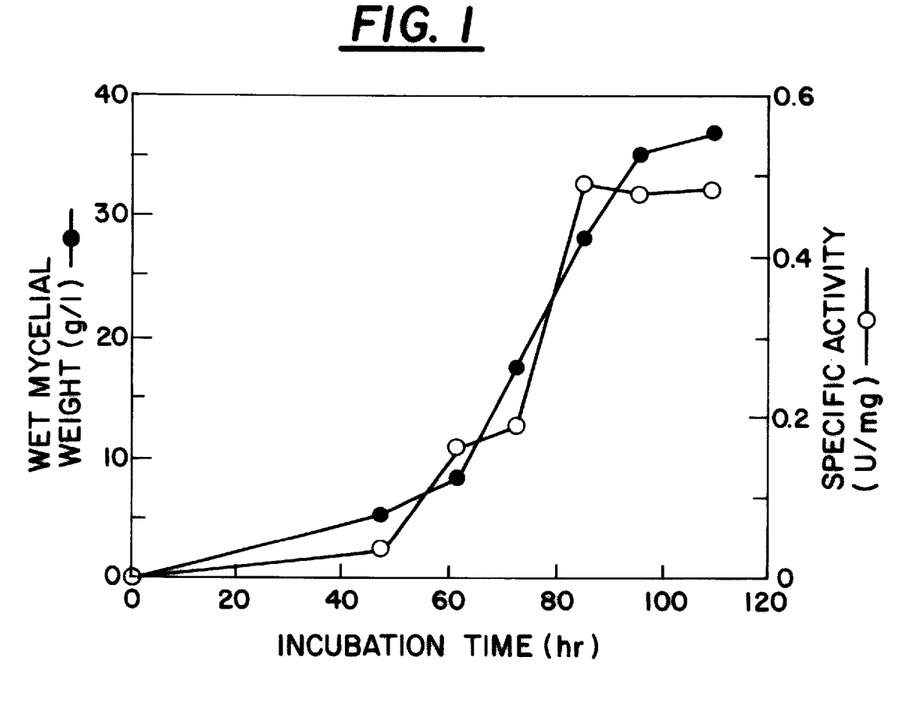
FIG. 1 is a graph showing a relation between the cultivation time and the amount of an FAOD-L produced in a culture medium.

The cultivation is normally conducted at temperature range of 25 to 37° C., preferably at 28° C. in a medium of pH range of 4.0 to 8.0, preferably 5.5 to 6.0. However, the culturing conditions may vary depending on various factors such as conditions of microorganisms and should not be limited to those described above. When cultivation is conducted for 20–100 hours under such conditions, an FAOD is accumulated in the culture medium (see, FIG. 1).

The resultant cultured medium is then treated in a conventional manner to remove nucleic acids, cell wall fragments, and the like, to yield an enzyme preparation.

Since the enzyme activity of FAODs of the present invention are normally accumulated in fungal cells, cells in the culture are harvested and ground to extract the enzyme.

The grinding of cells can be carried out in a conventional manner, for example, by means of mechanical grinding, autodigestion with a solvent, freezing, sonication, pressurization, or the like.

The method of isolation and purification of an enzyme is also known in the art. It can be conducted by combining known methods such as salting-out with ammonium sulfate, precipitation with an organic solvent such as ethanol, etc., ion-exchange chromatography, hydrophobic chromatography, gel filtration, affinity chromatography, and the like.

For example, mycelia are harvested by subjecting the resultant culture to centrifugation or suction filtration, washed, suspended in 0.1 M Tris-HCl buffer (pH 8.5), ground with Dyno-Mill and centrifuged. The supernatant as cell-free extract is then purified using, for example, fractionation with ammonium sulfate and phenyl-Sepharose hydrophobic chromatography.

For purposes of the present invention, the FAOD of the present invention may be any products or solutions obtainable throughout the total purification process irrespective of the purity of the enzyme, including the cultured medium, as far as they have the ability to catalyze the oxidization of amadori compounds as defined above. Further, any fragments of an enzyme molecule which are associated to the enzymatic activity having the ability to oxidize an amadori compound fall within the scope of the invention because such fragments are also useful for purposes of the present invention. The FAOD thus obtained is useful for determining amadori compounds, particularly, glycated proteins in the diagnosis of diabetes.

The present invention further provides a process for producing a fructosyl amino acid oxidase which comprises culturing a strain of the genus Aspergillus capable of producing a fructosyl amino acid oxidase in a medium containing at least either of fructosyl lysine and fructosyl-$N^\alpha$-Z-lysine and recovering a fructosyl amino acid oxidase from the cultured medium.

All the FAODs produced by such strains of the genus Aspergillus are useful for solving the technical problems which should be solved by the present invention.

The *Aspergillus terreus* GP1, which is a strain producing an FAOD-L of the present invention, is a novel fungus that has been isolated from the soil by the present inventors. The mycological characteristics of the strain are shown below.

(1) Growing Conditions in a Medium

It grows very well in Czapek agar medium or yeast MY medium. When cultured in a thermostatic chamber at 25° C. for 10 days, strains spread like velvet or, rarely, wool over Petri dish. The reversal side of colony is colorless or colored brown.

(2) Taxonomic Properties

The identification of isolated fungus was carried out through morphological observation as to conidia, conidiophore, conidial head, or the like, under microscopy after cultivating in Czapek agar medium. The observation revealed that the conidial head is in elongated cylindrical shape and colored brown or reddish brown. The conidiophore is smooth, colorless and slightly bending, and enlarged toward the tip to form a vesicle. The vesicle is hemispherical and colorless metulae can be observed at the upper half thereof. On the basis of these observation, the GP-1 strain was identified as *Aspergillus terreus*, which strain has been deposited at the "National Institute of Bioscience and Human-Technology, Agency of Industrial Science and Technology", 1-1-3, Higashi, Tsukuba-shi, Ibaraki-ken, Japan under the accession number FERM BP-5684 under the Budapest Treaty on Sep. 30, 1996 (original deposition date for domestic deposition is May 31, 1996).

The other strains, i.e., *Aspergillus terreus* IFO 6365 and *Aspergillus oryzae* IFO 4242, which produce FAOD-A of the present invention, have been deposited at and was released from, "INSTITUTE FOR FERMENTATION, OSAKA (IFO)", 17–85, Juso-honmachi 2-chome, Yodogawa-ku, Osaka-shi, Osaka 532, Japan, and have been deposited at the above-mentioned "National Institute of Bioscience and Human-Technology, Agency of Industrial Science and Technology", under the accession numbers FERM BP-5756 and 5757, respectively, under the Budapest Treaty on Nov. 25, 1996. Further, *Aspergillus oryzae* IFO 5710 has been deposited at the above-mentioned "INSTITUTE FOR FERMENTATION, OSAKA (IFO)" and can be deposited therewith in a publicly available manner for more than 30 years.

Characteristics of FLODs of the present invention will hereinafter be described in more detail.

1. Normal Induction Characteristics

The FAOD-L of the present invention is inducible with fructosyl lysine and/or FZL and is obtainable by culturing, for example, *Aspergillus terreus* GP1 in a medium containing fructosyl lysine and/or FZL as the nitrogen source and glucose as the carbon source.

The FAOD-A of the present invention is inducible with fructosyl lysine and/or FZL and is obtainable by culturing, for example, *Aspergillus terreus* IFO 6365 or *Aspergillus oryzae* IFO 4242 in a medium containing fructosyl lysine and/or FZL as the nitrogen source and glucose as the carbon source.

An FAOD can be induced in a GL brown-colored medium obtained by autoclaving glucose together with lysine and/or $N^\alpha$-Z-lysine but not in a medium containing glucose and lysine and/or $N^\alpha$-Z-lysine which have been autoclaved separately, which indicates that the enzyme is specific to amadori compounds.

2. Reaction- and Substrate-specificity

The FAOD of the present invention has a catalytic activity in the reaction below:

$$R^1\text{—CO—CH}_2\text{—NH—}R^2 + O_2 + H_2O \rightarrow R^1\text{—CO—CHO} + R^2\text{—NH}_2 + H_2O_2$$

wherein $R^1$ is an aldose residue and $R^2$ is an amino acid, protein or peptide residue.

In the above reaction scheme, amadori compounds of the formula $R^1$—CO—CH$_2$—NH—$R^2$ wherein $R^1$ is —OH, —(CH$_2$)$_n$— or —[CH(OH)]$_n$—CH$_2$OH (n is an integer of 0 to 6) and $R^2$ is —CHR$^3$—[CONHR$^3$]$_m$COOH ($R^3$ is a side chain residue of an α-amino acid and m is an integer of 1 to 480) are preferred as substrate. Among them, compounds wherein $R^3$ is a side chain residue of an amino acid selected from lysine, poly-lysine, valine, asparagine, etc., n is 5 to 6 and m is 55 or less are more preferred.

Strains capable of producing FAOD of the present invention are listed in Table 1 below.

TABLE 1

Substrate specificity of FAOD purified from a strain of the genus Aspergillus in FZL brown-colored medium

| Strain | Relative activity (10$^{-2}$U/ml) | | |
|---|---|---|---|
| | FZL[1] | FV | LV[2] |
| A. terreus IFO6365 (FERM BP-5756) | 104 | 12.4 | 8.4 |
| A. oryzae IFO4242 (FERM BP-5757) | 16.9 | 3.9 | 4.4 |
| A. oryzae IFO5710 | 34.4 | 5.8 | 6.0 |
| A. terreus GP1 (FFRM BP-5684) | 20.6 | 10.4 | 2.0 |

[1]Fructosyl N$^{\alpha\text{-Z-lysine}}$
[2](Activity on fructosyl lysine)/(activity on fructosyl valine)

As is apparent from Table 1, FAODs of the present invention are characteristically specific to fructosyl-lysine and valine to a similar extent or more specific to the former, indicating that the FAOD is useful in the determination of glycated protein.

Substrate specific activity of the FAOD-A produced by A. terreus IFO6365 is shown in Table 2 below.

TABLE 2

Substrate specificity of FAOD-A originated from A. terreus IFO6365

| Substrate | Concentration | Specific activity (%) |
|---|---|---|
| N$^\epsilon$-fructosyl N$^\alpha$-Z-lysine | 1.67 mM | 100 |
| Fructosyl valine | 1.67 mM | 20.5 |
| N$^\epsilon$Methyl-L-lysine | 1.67 mM | N.D[1] |
| N$^\epsilon$-Fructosylpoly-L-lysine | 0.02% | 2.0 |
| Poly-L-lysine | 0.02 | N.D. |
| FBSA[2] | 0.17 | N.D. |
| FHSA[3] | 0.17 | N.D. |
| Tryptic FBSA | 0.17 | N.D. |
| Tryptic FHSA | 0.17 | N.D. |

[1]Not detected
[2]Fructosyl bovine serum albumin
[3]Fructosyl human serum albumin As is apparent from Table 2, the FAOD-A of the present invention is active on fructosyl lysine and fructosyl valine, and also fructosyl polylysine, indicating that the said enzyme is useful in the determination of glycated hemoglobin, too.

Specific activity of an FAOD-L produced by A. terreus GP1 is shown in Table 3 below.

TABLE 3

Substrate specificity of FAOD-L originated from A. terreus GP1

| Substrate | Concentration | Specific activity (%) |
|---|---|---|
| N$^\epsilon$-Fructosyl N$^\alpha$-Z-lysine | 1.67 mM | 100 |
| Fructosyl valine | 1.67 mM | 32.1 |
| N$^\epsilon$-Methyl-L-lysine | 1.67 mM | N.D[1] |
| N$^\epsilon$-Fructosylpoly-L-lysine | 0.02% | 0.30 |
| Poly-L-lysine | 0.02 | N.D. |
| FBSA[2] | 0.17 | N.D. |
| FHSA[3] | 0.17 | N.D. |
| Tryptic FBSA | 0.17 | 0.58 |
| Tryptic FHSA | 0.17 | N.D. |

[1]Not detected
[2]Fructosyl bovine serum albumin
[3]Fructosyl human serum albumin As is apparent from Table 3, the FAOD-L of the present invention is active on fructosyl lysine and fructosyl valine, and also fructosyl polylysine. Further, it has been proved to be active on protease-treated protein, and, therefore, is useful in the determination of glycated hemoglobin.

3. Evaluation of Titer

Titration of an enzyme was carried out as follows:

(1) Method based on the colorimetric determination of the resultant hydrogen peroxide A. Measurement of Generation Rate A 100 mM FZL solution was prepared by dissolving previously-obtained FZL in distilled water. To 100 μl of 45 mM 4-aminoantipyrine, 100 μl of 60 U/ml peroxidase, 100 μl of 60 mM phenol, 1 ml of 0.1 M Tris-HCl buffer (pH 8.0) and 50 μl of enzyme solution was added distilled water to total volume of 3.0 ml. The mixture was incubated at 30° C. for 2 minutes, 50 μl of 100 mM FZL solution was added thereto, and the time course of absorbance at 505 nm was measured. The amount (μmole) of hydrogen peroxide generated per minute was calculated on the basis of molar absorptivity (5.16×10$^3$ M$^{-1}$cm$^{-1}$) of quinone pigment produced, and the resultant numerical value was taken as a unit(U) of enzyme activity.

B. End Point Method

Procedures similar to those described above are repeated and, after the addition of a substrate, the mixture was incubated for 30 minutes. The absorbance at 505 nm was measured. The enzyme activity was evaluated on the basis of the amount of hydrogen peroxide generated referring to a calibration curve previously obtained using a standard hydrogen peroxide solution.

(2) Method based on the oxygen absorption due to enzyme reaction

To a mixture of 1 ml of 0.1 M Tris-HCl buffer (pH 8.0) and 50 μl of an enzyme solution was added distilled water to obtain a solution of a total volume of 3.0 ml. The resulting solution was charged in a cell of an oxygen electrode manufactured by Lank Brothers Co. The solution was stirred at 30° C. to allow the dissolved oxygen to be equilibrated under the temperature and 100 μl of 50 mM FZL was added thereto. Then, the oxygen absorption was continuously measured on a recorder to obtain an initial rate. The amount of oxygen absorbed for one minute was determined on the basis of a calibration curve, which was taken as an enzyme unit.

4. pH and Temperature Conditions

Determination of pH condition:

The optimum pH was determined in accordance with the general method for the determination of the FAOD activity (see, "3. Evaluation of titer, (1), A. above), except that the enzymatic reaction is conducted in a buffer of pH between 5–11 such as 0.1 M potassium phosphate buffer (KPB), Tris-HCl buffer or glycine-NaOH buffer.

Stability against pH was evaluated by adding FAOD to each of the above-mentioned buffers, incubating for 30 minutes at 30° C., and determining the activity under the normal condition (30° C., pH 8.0).

Determination of temperature condition

The optimum temperature was determined by allowing to react at temperature range of 20–60° C. The stability against temperature was determined by incubating a solution of FAOD dissolved in 0.1M Tris-HCl buffer (pH 8.0) for 10 minutes at various temperature between 20–60° C., and measuring the residual activity of the enzyme solution under the normal condition.

Figure 2:
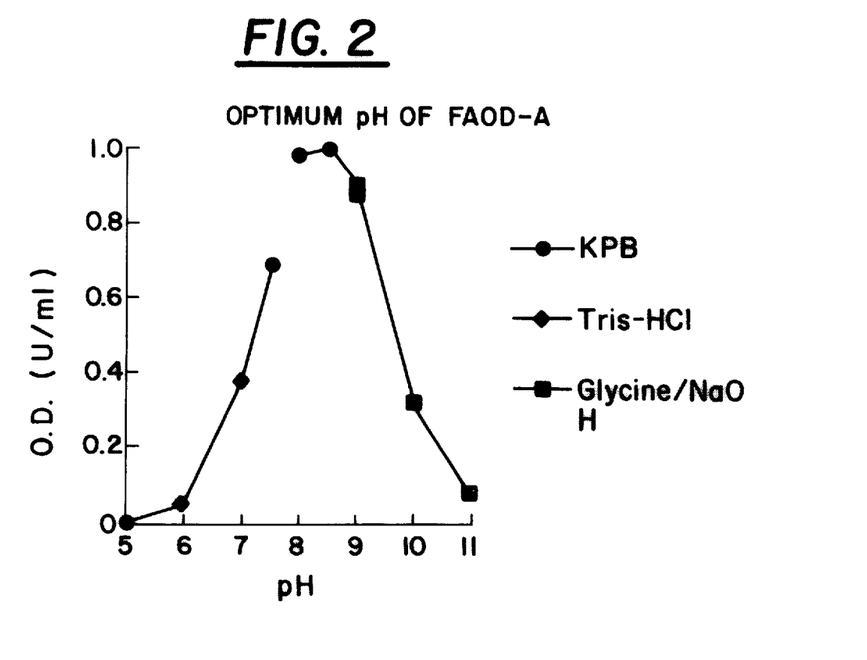
FIG. 2 is a graph showing a relation between the optimum pH and the activity of an FAOD-A.
Figure 3:
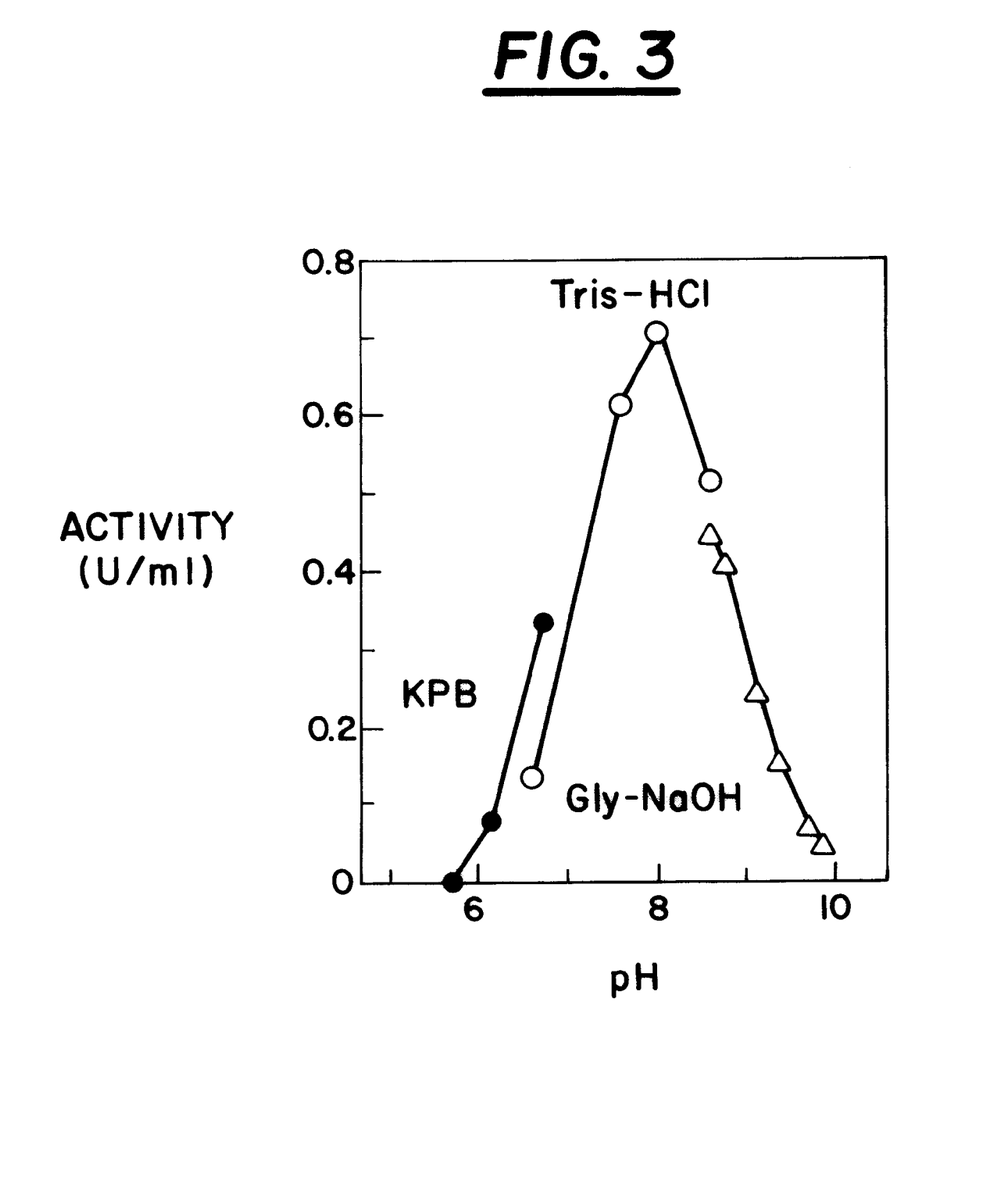
FIG. 3 is a graph showing a relation between the optimum pH and the activity of an FAOD-L.

When evaluated by the methods above, the optimum pH of FAOD-A of the present invention is 7.5–9.0, preferably 8.5 (FIG. 2), and it is stable at pH 7.0–10.0. The optimum pH of FAOD-L is 7.5–9.0, preferably 8.0 (FIG. 3), and it is stable at pH 4.0–13.0.

Figure 4:
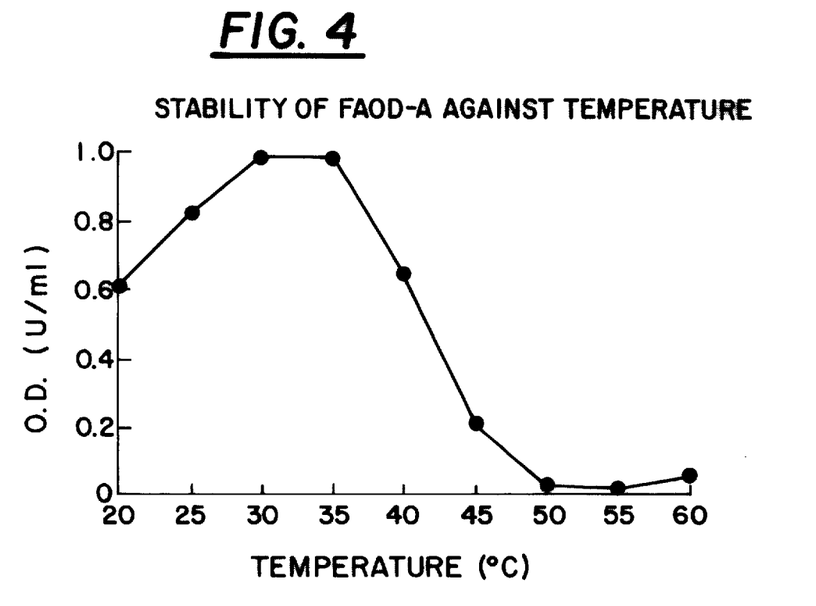
FIG. 4 is a graph showing a relation between the optimum temperature and the activity of an FAOD-A.
Figure 5:
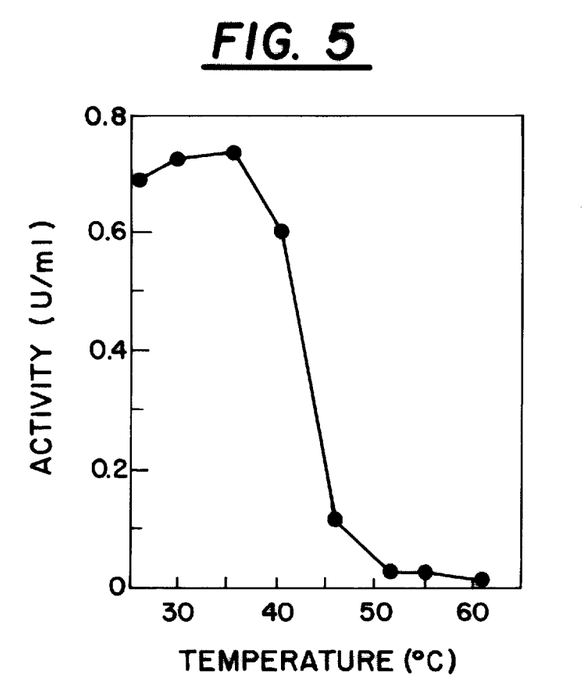
FIG. 5 is a graph showing a relation between the optimum temperature and the activity of an FAOD-L.

In the case of FAOD-A, the enzyme reaction proceeds efficiently at 20–40° C., preferably 35° C. (FIG. 4), and the enzyme is stable at 20–40° C. In the case of FAOD-L, the enzyme reaction proceeds efficiently at 20–50° C., preferably 25–40° C., more preferably 35° C. (FIG. 5), and the enzyme is stable at 20–50° C.

5. Comparison with Known Enzymes

The FAOD of the present invention was compared with known fructosyl amino acid oxidases derived from various microorganisms.

TABLE 4

Comparison of Fructosyl amino acid oxidases derived from various microorganisms

| Strain | Specific activity (unit/mg) | |
|---|---|---|
| | FL | FV |
| Corynebacterium sp.[1] | 0[4] | 100 |
| Aspergillus sp.[2] | 13[3] | 100 |
| A. terreus IFO6365 FERM BP-5756 | 839[5] | 100 |
| A. oryzae IFO4242 FERM BP-5757 | 437[5] | 100 |
| A. oryzae IFO5710 | 598[5] | 100 |
| A. terreus GP1 FERM BP-5684 | 312 | 100 |

FL: fructosyl lysine
FV: fructosyl valine
[1]T. Horiuchi et al., Agric. Biol. Chem., 53(1), 103–110 (1989)
[2]Japanese Patent Publication (KOKAI) 3-155780
[3]Relative activity where the activity on fructosyl valine is estimated to be 100.
[4]Activity on $N^\epsilon$-D-fructosyl-L-lysine
[5]Activity on $N^\epsilon$-Z-L-lysine As is apparent from Table 4, the following differences can be noted between the FAOD of the present invention and those derived from two other strains. That is, the FAOD obtainable according to the present invention is more active on fructosyl lysine than fructosyl valine, while the enzyme derived from genus Corynebacterium does not act on fructosyl lysine and the enzyme derived from Aspergillus sp. described in Japanese Patent Publication (KOKAI) 3-155780 is less active on fructosyl lysine compared to fructosyl valine.

6. Molecular Weight of FAOD-A and FAOD-L

Molecular weight of the FAOD-A and FAOD-L is determined by Superdex 200 pg.

The results are shown in Table 5.

TABLE 5

Molecular weight of FAOD-A and FAOD-L

| Enzyme derived from | M.W. |
|---|---|
| A. terreus IFO6365 FERM BP-5756 | 50,000 |
| A. terreus GP1 FERM BP-5684 | 94,000 |

As is apperent from Table 5, the FAOD-A and FAOD-L of the present invention have different molecular weight and are distinct from each other.

7. Inhibition, Activation and Stabilization of Enzyme (1) Effect of Metal Ions

To an enzyme solution was added a solution containing a metal ion to be tested at a final concentration of 1 mM in 0.1 M Tris-HCl buffer (pH 8.0). After 5-minute-incubation at 30° C., the enzyme activity was assayed. The results are shown in Tables 6 and 7 below.

TABLE 6

Effect of metal ion on the activity of FAOD-A

| Material (1 mM) | relative activity (%) | material (1 mM) | relative activity |
|---|---|---|---|
| None | 100 | $FeSO_4$ | N.D. |
| LiCl | 103 | $COSO_4$ | 54 |
| KCl | 105 | $CuCl_2$ | 105 |
| NaCl | 104 | $ZnSO_4$ | 35 |
| RbCl | 107 | $AgNO_3$ | N.D. |
| CsCl | 108 | $BaCl_2$ | 115 |
| $MgCl_2$ | 108 | $HgCl_2$ | 31 |
| $CaCl_2$ | 104 | $FeCl_3$ | 100 |
| $MnCl_2$ | 59 | | |

N.D.: not detectable due to turbidity

It is apparent from Table 6 that the FAOD-A of the present invention is inhibited by zinc and mercury ions, and the manganese and cobalt ions are also inhibitory.

TABLE 7

Effect of metal ion on the activity of FAOD-L

| Material (1 mM) | relative activity (%) | material (1 mM) | relative activity |
|---|---|---|---|
| None | 100 | $FeSO_4$ | 95 |
| LiCl | 98 | $CoSO_4$ | 107 |
| KCl | 102 | $CuCl_2$ | 38 |
| NaCl | 113 | $ZnSO_4$ | 14 |
| RbCl | 107 | $AgNO_3$ | 0 |
| CsCl | 107 | $BaCl_2$ | 113 |
| $MgCl_2$ | 101 | $HgCl_2$ | 0 |
| $CaCl_2$ | 96 | $FeCl_2$ | 80 |
| $MnCl_2$ | 101 | | |

It is apparent from Table 7 that the FAOD-L of the present invention is inhibited completely by silver and mercury ions and the copper and zinc ions are inhibitory.

(2) Effect of Various Inhibitors

The inhibitory effect of various substances was tested in a manner substantially analogous to that described in (1) above. In the present test, the final concentration of parachloro mercuric benzoate (PCMB) is 0.1 mM while that of others 1 mM. The results are shown in Tables 8 and 9.

TABLE 8

Effect of various inhibitors on FAOD-A activity

| Material (1 mM) | relative activity (%) | material (1 mM) | relative activity |
|---|---|---|---|
| None | 100 | semicarbazide | 64 |
| p-CMB[1] | 2 | phenylhydrazine | 0 |
| DTNB[2] | 7 | hydrazine | 10 |
| Acetic iodide | 66 | hydroxylamine | 10 |
| NaN$_3$ | 68 | Clorgyline | N.D. |
| α,α-Dipyridyl | 67 | aminoguanidine | 60 |
| α-Phenanthroline | 62 | | |

[1] p-CMB, parachloro mercuric benzoate.
[2] DTNB, 5,5'-Dithiobis(2-nitrobenzoic acid).
N.D.: not detectable due to turbidity It is apparent from Table 8 that p-CMB, DTNB, hydrazine and phenylhydrazine inhibit the FAOD-A activity completely.

TABLE 9

Effect of various inhibitors on FAOD-L activity

| Material (1 mM) | relative activity (%) | material (1 mM) | relative activity |
|---|---|---|---|
| None | 100 | semicarbazide | 94 |
| p-CMB[1] | 0 | phenylhydrazine | 52 |
| DTNB[2] | 0 | hydrazine | 9 |
| Acetic iodide | 88 | hydroxylamine | 2 |
| NaN$_3$ | 105 | Clorgyline | N.D.[3] |
| α,α-Dipyridyl | 102 | deprenyl | 106 |
| o-Phenanthroline | 111 | aminoguanidine | 69 |

[1] p-CMB, parachloro mercuric benzoate.
[2] DTNB, 5,5'-Dithiobis(2-nitrobenzoic acid).
[3] N.D., not detectable due to turbidity

It is apparent from Table 8 that p-CMB, DTNB and hydrazine inhibit the FAOD-L activity strongly.

These results indicate that an SH- or carbonyl-group plays an important role in the enzymatic reaction by FAOD. Accordingly, a buffer (pH 7.5–9.0) containing 1 to 2 mM dithiothreitol is suited for the preservation of FAOD.

Figure 6:
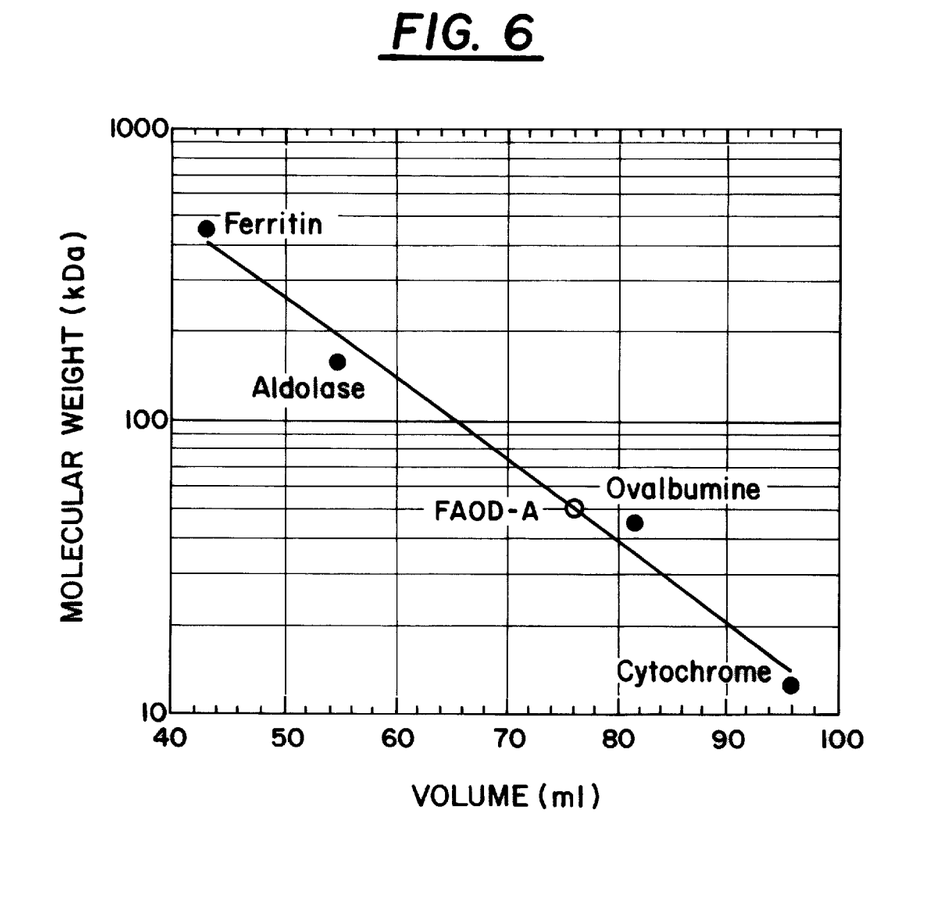
FIG. 6 is a graph showing the molecular weight of an FAOD-A purified from *A. terreus* IFO 6365 (FERM BP-5756) determined by gel filtration on Superdex 200 pg.
Figure 9:
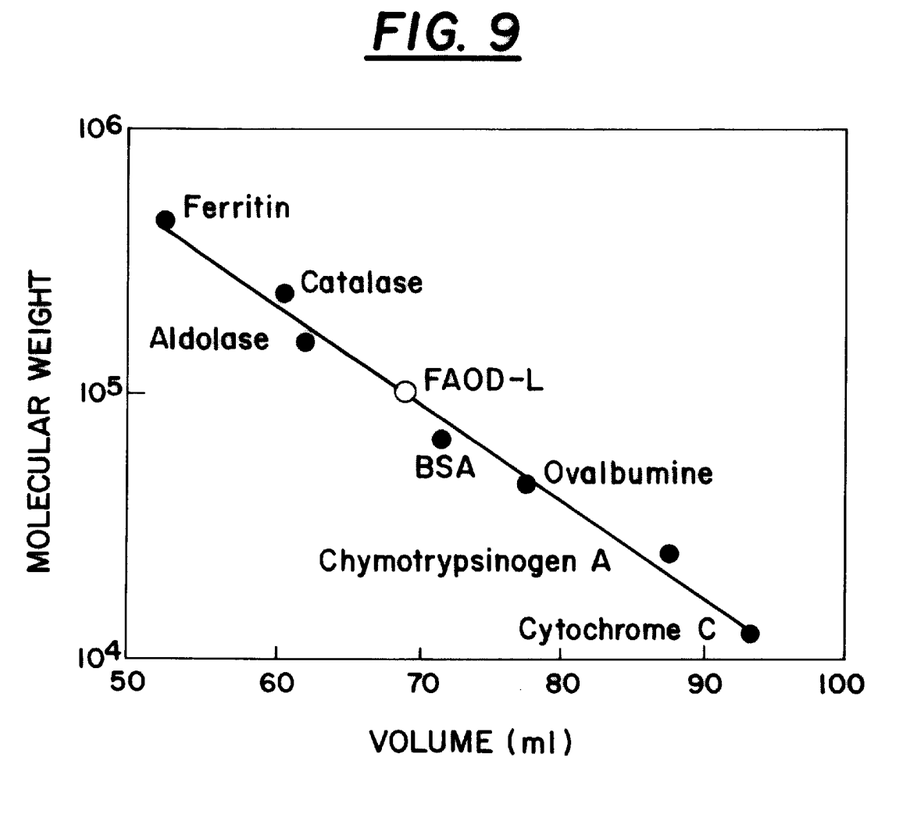
FIG. 9 is a graph showing the measurement of molecular weight of an FAOD-L purified from *A. terreus* GP1 (FERM BP-5684) by gel filtration on Superdex 200 pg.

Molecular weight of the FAOD-A, when determined by gel filtration on Superdex 200 pg [column, Superdex 200 pg HR16/60; buffer, 0.2 M potassium phosphate (pH 7.0); flow rate, 1 ml/min; sample, a solution containing 0.5 mg of each protein in 0.2 ml of sample buffer], was estimated to be about 50,000 (50 kDa). See, FIG. 6. Molecular weight of the FAOD-L, when determined in a similar manner, was estimated to be about 94,000 (94 kDa). See, FIG. 9.

As discussed above, the FAOD of the present invention is useful in an assay of amadori compounds. Accordingly, the present invention provides an assay of an amadori compound in a sample, which comprises bringing the sample containing an amadori compound into contact with the FAOD of the present invention and determining the amount of oxygen consumed or that of hydrogen peroxide produced. The assay of the present invention is carried out on the basis of the measurement of the amount of glycated protein and/or glycation rate, or the determination of fructosyl amine in a sample derived from a living body.

The enzyme activity of an FAOD is evaluated by the following reaction scheme:

wherein $R^1$ is an aldose residue and $R^2$ is an amino acid, protein or peptide residue.

As a sample solution to be tested, there can be used any solutions containing an amadori compound(s), for example, those derived from food products such as soy sauce, etc. as well as those derived from a living body such as blood (e.g. whole blood, plasma or serum), urine, or the like.

The FAOD of the present invention is allowed to react with a sample containing an amadori compound in a suitable buffer. The suitable pH and temperature of the reaction mixture can be pH 6.0–10.0, preferably 8.5, and 20–50° C., preferably 35° C., respectvely, for FAOD-A; and pH 7.0–9.0, preferably 8.5, and 25–40° C., preferably 35° C., respectively, for FAOD-L. As a buffer, Tris-HCl can be used. The amount of FAOD to be used in an assay is normally 0.1 unit/ml or more, preferably 1 to 100 units/ml in the case of end point method.

In the present assay, the amadori compounds are determined according to any one of the following methods.

(1) Method based on the amount of hydrogen peroxide generated

The hydrogen peroxide is measured according to any one of known methods for determining hydrogen peroxide such as colorimetric method or a method utilizing a hydrogen peroxide electrode. The amadori compounds in the sample is then estimated on the basis of the measurement in reference to a calibration curve showing the relation between the amount of hydrogen peroxide and that of amadori compounds. Specifically, the determination can be conducted in a manner similar to that described in "3. Evaluation of Titer", except that the amount of FAOD is 1 unit/ml and that a sample to be tested is diluted before the measurement of hydrogen peroxide produced.

Any color-developing system for hydrogen peroxide can be used in the present method on condition that it leads to the color-development due to oxidative condensation between a chromogen such as phenol and a coupler such as 4-aminoantipyrine, 3-methyl-2-benzothiazolinone hydrazone in the presence of peroxidase.

Examples of chromogen include phenolic derivatives, aniline derivatives and toluidine derivatives, for example, N-ethyl-N-(2-hydroxy-3-sulfopropyl)-m-toluidine, N,N-dimethylaniline, N,N-diethylaniline, 2,4-dichlorophenol, N-ethyl-N-(2-hydroxy-3-sulfopropyl)-3,5-dimethoxyaniline, N-ethyl-N-(3-sulfopropyl)-3,5-dimethylaniline, and N-ethyl-N-(2-hydroxy-3-sulfopropyl)-3,5-dimethylaniline. A leuco-type color-developing agent which develops color upon oxidation in the presence of peroxidase is also available. Such "leuco-type color developing agents" are known in the art and examples thereof include o-dianisidine, o-tolidine, 3,3-diaminobenzidine, 3,3,5,5-tetramethylbenzidine, N-(carboxymethylaminocarbonyl)-4,4-bis(dimethylamino) biphenylamine, 10-(carboxymethylaminocarbonyl)-3,7-bis (dimethylamino)phenothiazine, and the like.

(2) Method based on the amount of oxygen consumed

Amadori compound in a sample can be estimated from the amount of oxygen consumed, which is calculated by subtracting the amount of oxygen at the completion of reaction from the one at the beginning of the reaction in reference to a calibration curve concerning the relation of the amount of oxygen consumed and that of amadori compounds. Specifically, it can be conducted in a manner similar to the titration described in "3. Evaluation of titer" above, except that the amount of FAOD is 1 unit/ml and that a sample to be added is previously diluted appropriately before the measurement of oxygen consumed.

According to the assay of the present invention, a sample solution can be used as it is or can be subject to pre-treatment so as to liberate lysine and/or valine residue to which a sugar is bound, depending on the type of the glycated protein.

For such a purpose, the sample is treated with a protease (enzymatic method) or a chemical substance such as hydrochloric acid, etc. (chemical method). In the case of enzymatic method, proteases of endo- and exo-type known in the art can be used in the process of the present invention. Examples of endo-type protease include trypsin, α-chymotrypsin, subtilisin, proteinase K, papain, cathepsin B, bromelin, pepsin, thermolysin, protease XIV, lysylendopeptidase, proleser and bromelin F. Examples of exo-type protease include aminopeptidase and carboxypeptidase. The method of the enzyme treatment is also known.

As mentioned above, the FAOD of the present invention is specific to fructosyl lysine in a glycated lysine, and, therefore, is useful in the diagnosis of diabetes, which comprises determining glycated protein in a blood sample. The enzyme is also specific to fructosyl valine, and, therefore, is useful in the determination of glycated hemoglobin too.

When blood (e.g. whole blood, plasma or serum) is to be assayed, a blood sample derived from a living body can be used as it is or after pre-treatment such as dialysis, etc.

Further, enzymes (e.g. FAOD, peroxidase, etc.) can be in a liquid- or immobilized form on an appropriate solid support. For example, a column packed with enzyme immobilized onto beads can be used to obtain an automated device which must improve the efficiency of a routine assay such as clinical examination where a lot of specimens must be tested in accuracy and rapidity. The immobilized enzyme has another advantage in view of economical efficiency because it can be used repeatedly.

Furthermore, it is possible to provide a kit by combining an enzyme(s) with a color-developing reagent(s) in an appropriate manner, which kit is useful for both of clinical assay and food analysis of amadori compounds.

The immobilization of the enzyme can be conducted by a method known in the art. For example, it is conducted by a carrier bonding method, cross-linkage method, inclusion method, complexing method, and the like. Examples of carriers include polymer gel, microcapsule, agarose, alginic acid, carrageenan, and the like. The enzyme can be bound to a carrier through covalent bond, ionic bond, physical absorption, biochemical affinity, etc. according to a method known in the art.

When using an immobilized enzyme, the assay may be carried out in flow or batch system. As described above, the immobilized enzyme is particularly useful for a routine assay (clinical examination) of glycated proteins in blood samples. In the clinical examination for the diagnosis of diabetes, the result as criterion for diagnosis is expressed in concentration of glycated protein, glycation rate which is the ratio of the concentration of glycated protein to that of whole protein in the sample, or the fructosamine value. The whole protein concentration can be determined in a conventional manner, for example, through the measurement of absorbance at 280 nm, Bradford method, Lowry method, bullet method, natural fluorescence of albumin, or the absorbance of hemoglobin.

The present invention also provides a reagent or a kit used in an assay of amadori compounds, which comprises an FAOD of the present invention. The reagent comprises an FAOD and a buffer whose pH is preferably 7.0 to 9.0, more preferably 8.0 to 8.5. When the FAOD is immobilized, the solid support can be selected from a polymer gel, and the like, and alginic acid is preferred.

In the case of end point assay, the reagent usually contains 1 to 100 units/ml of FAOD for each sample, and Tris-HCl buffer (pH 8.0–8.5).

When amadori compounds are assayed on the basis of generated hydrogen peroxide, any of the color-developing systems which develop color due to oxidative condensation, leuco-type color-developing agents, and the like, can be used, as described in "(1) Method based on the amount of the hydrogen peroxide generated" above.

The reagent used in an assay of amadori compound of the present invention may be combined with a suitable color-developing agent together with a color criterion or a standard substance to give a kit which is useful for a preliminary diagnosis or examination.

The reagent or the kit described above is used for measurement of the amount of glycated protein and/or glycation rate or the determination of fructosamine in a sample derived from a living body.

The following Examples further illustrate the present invention in detail.

Example 1

Fermentation of *A. terreus* and Purification of FAOD-A

1) Fermentation

*A. terreus* IFO6365 (FERM BP-5756) was inoculated into a medium (pH 6.0, 7 L) containing 0.5% FZL, 1.0% glucose, 0.1% $K_2HPO_4$, 0.1% $NaH_2PO_4$, 0.05% $MgSO_4$, 0.01% $CaCl_2$ and 0.2% yeast extract, and grown at 28° C. for 80 hours with shaking using a jar fermentor. The culture was filtered to harvest mycelia.

2) Preparation of Crude Extract

A portion of mycelia (100 g, wet weight) was suspended in 0.1 M Tris-HCl buffer (pH 8.0, 200 ml) containing 2 mM DTT, 1/2 volume of zirconium beads and ground with a beadbeater for 1 minute followed by ice-cooling (2×) for 1 minutes, i.e., 3 minutes in total. The ground mixture was centrifuged at 9,500 rpm, 4° C. for 10 minutes to obtain the supernatant (cell-free extract) as a crude extract, which was then subjected to the purification as shown below.

3) Purification

Step 1: Sodium sulfate fractionation

To the crude extract was added ammonium sulfate to 40% saturation and the mixture was centrifuged at 12,000 rpm, 4° C. to remove the contaminating proteins. To the supernatant was added ammonium sulfate to 80% saturation to recover the pellets.

Step 2: Ion-exchange chromatography

The precipitates obtained in step 1 were dissolved in 50 mM potassium phosphate buffer containing 2 mM DT-T (hereinafter, referred to as "buffer A") and the solution was dialyzed overnight against the buffer A. The resultant enzyme solution was applied to DEAE-TOYOPEARL column equilibrated with the buffer A. The column was eluted with a linear gradient of 0–0.5 M potassium chloride. The active fractions were pooled, concentrated with ammonium sulfate, and subjected to the next step.

Step 3: Hydrophobic chromatography

The recovered active fractions were applied to a phenyl TOYOPEARL column equilibrated with the buffer A containing 40% sodium sulfate. The concentrate was allowed to adsorb on the column and washed with the buffer. The active fractions were obtained using a linear gradient of containing 40-0% sodium sulfate.

Step 4: Gel filtration

Finally, the gel filtration was carried out using Superdex 200 pg equilibrated with 20 mM phosphate buffer (pH 7.5) containing 2 mM DTT, which gave an enzyme preparation of about 10 units. The enzyme preparation was tittered according to the method described in "3. Evaluation of titer, (1), A" above.

Determination of molecular weight

Molecular weight, when determined by gel filtration on Superdex 200 pg [column, Superdex 200 pg HR16/60; buffer, 0.2 M potassium phosphate (pH 7.0); flow rate, 1 ml/min; sample, a solution containing 0.5 mg of each protein in 0.2 ml of sample buffer], was estimated to be about 50,000 (50 kDa). See, FIG. 6.

Example 2

Fermentation of A. terreus GP1 and Purification of FAOD-L

1) Fermentation

A. terreus GP1 (FERM BP-5684) was inoculated into a medium (pH 6.0, 10 L) containing 0.5% FZL, 1.0% glucose, 0.1% $K_2HPO_4$, 0.1% $NaH_2PO_4$, 0.05% $MgSO_4$, 0.01% $CaCl_2$ and 0.2% yeast extract, and grown at 28° C. for 80 hours while aerating at 2 L/min and stirring at 400 rpm using a jar fermentor. The culture was filtered to harvest mycelia.

2) Preparation of Crude Extract

A portion of mycelia (270 g, wet weight) was suspended in 0.1 M Tris-HCl buffer (pH 8.5, 800 ml) containing 2 mM DTT and ground with Dino-Mill. The ground mixture was centrifuged at 9,500 rpm for 20 minutes to obtain the supernatant (cell-free extract) as a crude extract, which was then subjected to the purification as shown below.

3) Purification

Step 1: Sodium sulfate fractionation

To the crude extract was added ammonium sulfate to 40% saturation and the mixture was centrifuged at 12,000 rpm, 4° C. to remove the contaminating proteins. To the supernatant was added ammonium sulfate to 75% saturation to recover the pellets.

Step 2: Hydrophobic chromatography (Batch method)

The precipitates obtained in step 1 were dissolved in 50 mM Tris-HCl buffer (pH 8.5) containing 2 mM DTT (hereinafter, referred to as "buffer A"). To the solution was added the equal amount of buffer A containing 40% sodium sulfate. The crude enzyme solution was allowed to adsorb onto 200 mg of butyl-TOYOPEARL resin by batch method. The resin was eluted by batch method with buffer A and the active fractions were concentrated with ammonium sulfate.

Step 3: Hydrophobic chromatography

The concentrated active fractions were allowed to adsorb onto a phenyl TOYOPEARL column equilibrated with the buffer A containing 25% sodium sulfate. The column was washed with the same buffer and eluted with a linear gradient of 25–0% sodium sulfate. The recovered active fractions were concentrated with sodium sulfate precipitation and used in the next step.

Step 4: Hydrophobic chromatography

The recovered active fractions were subjected to a butyl TOYOPEARL column equilibrated with the buffer A containing 40% sodium sulfate. The column to which the concentrate was adsorbed was washed with the same buffer. The active fractions were obtained with a linear gradient containing 40–0% sodium sulfate.

Step 5: Ion-exchange chromatography

The purification was then conducted by DEAE TOYOPEARL column chromatography equilibrated with buffer A. The washings containing FAOD activity was pooled and concentrated with sodium sulfate. The concentrate was used in the next step.

Step 6: Gel filtration

Finally, the gel filtration was carried out using Sephacryl 300 equilibrated with 0.1 M Tris-HCl buffer (pH 8.5) containing 0.1 M NaCl and 2 mM DTT, which gave an enzyme preparation of 70–100 units.

Figure 7:
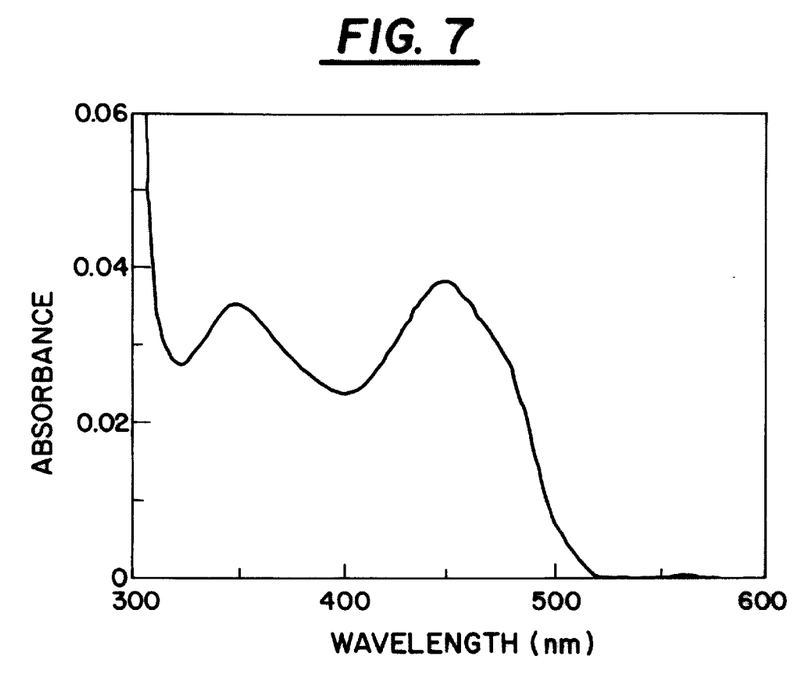
FIG. 7 shows the UV absorption spectrum of an FAOD purified from *Aspergillus terreus* GP1 (FERM BP-5684).

The UV absorption spectrum of purified FAOD is shown FIG. 7. The FIG. 7 indicates that the said enzyme is a flacon enzyme.

The purified enzyme preparation was subjected to the determination of molecular weight by SDS-PAGE (sodium dodecyl sulfate polyacrylamide gel electrophoresis) and gel filtration using Superdex 200 pg.

Figure 8:
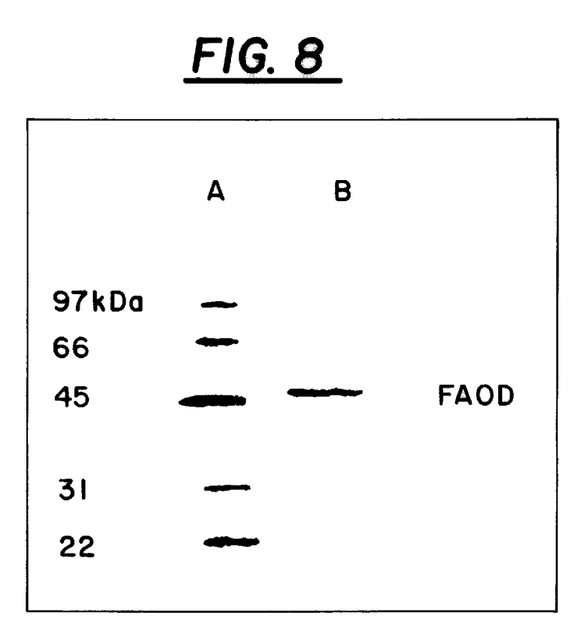
FIG. 8 is a copy of a picture showing the results of the migration pattern of SDS-PAGE (dodecyl sulfate-polyacrylamide gel electrophoresis) of an FAOD-L purified from *A. terreus* GP1 (FERM BP-5684).

The SDS-PAGE was effected according to the Davis's method using 10% gel at 40 mA for 3 hours and staining proteins with Coomassie brilliant blue G-250. Molecular weight marker was obtained by electrophoresing standard proteins including phosphorylase B, bovine serum albumin, ovalbumin, carbonic anhydrase and soybean trypsin inhibitor simultaneously. The molecular weight of a subunit of FAOD proved to be about 48,000 (48 kDa). See, FIG. 8.

The gel filtration was effected using 0.1 M Tris-HCl buffer (pH 8.5) containing 0.1 M NaCl, which revealed the molecular weight to be about 94,000 (94 kDa). See, FIG. 9.

EXAMPLE 3

Determination of Glycated Human Albumin

A series of glycated human albumin solutions of different concentration between 0 and 10% were prepared by dissolving glycated human serum albumin (Sigma) in 0.9% sodium chloride solution. The solutions were then used in the determination as follows.

1) Protease Treatment

A mixture of a glycated albumin solution (60 μl) and 12.5 mg/ml protease XIV (Sigma) solution (60 μl) was incubated at 37° C. for 30 minutes. The mixture was then heated at about 90° C. for 5 minutes to stop the reaction.

2) Determination of Activity

An FAOD reaction mixture was prepared by mixing 45 mM 4-aminoantipyrine solution (30 μl), 60 mM N-ethyl-N-(2-hydroxy-3-sulfopropyl)-m-toluidine solution (30 μl), peroxidase solution (60 units/ml) (30 μl), 0.1 M Tris-HCl buffer (pH 8.0) (300 μl) and FAOD-L solution (6 units/ml) (50 μl), and adjusting the total volume to 1 ml with distilled water.

The FAOD-L solution (6 units/ml) was prepared by diluting the purified FAOD-L obtained in Example 2 with 0.1 M Tris-HCl buffer (pH 8.0).

Figure 10:
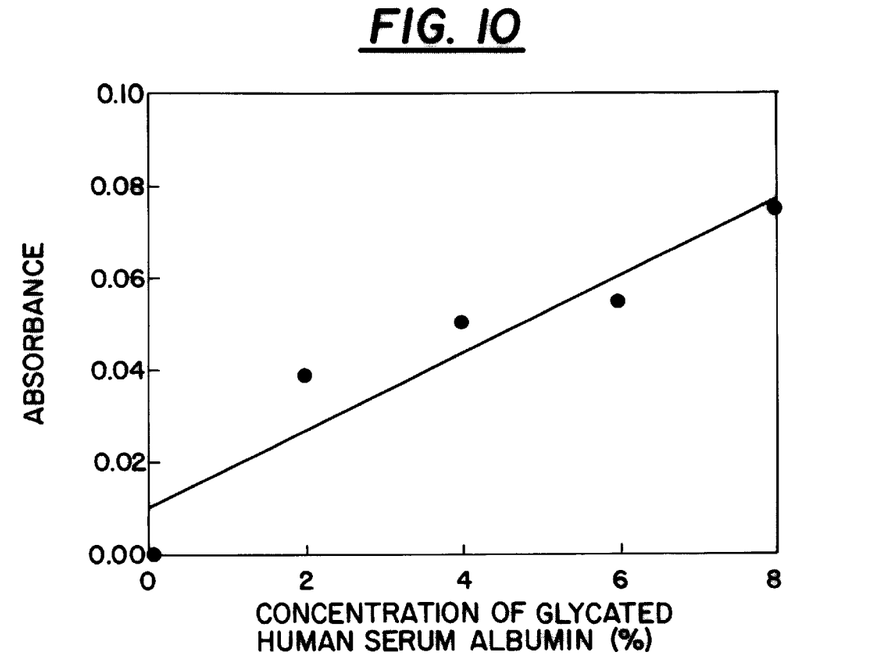
FIG. 10 is a graph showing the relation between the concentration of glycated human serum albumin and the amount of hydrogen peroxide produced due to the action of an FAOD-L.

The FAOD reaction mixture was incubated for 2 minutes at 30° C. for 2 minutes, and each of protease-treated solution (100 μl) was added thereto. Thirty minutes later, the absorbance at 555 nm was measured. The relationships between the glycated albumin concentration and the absorbance are shown in FIG. 10, wherein the ordinate indicates the absorbance at 555 nm, which corresponds to the amount of hydrogen peroxide generated, and the abscissa the concentration of glycated albumin. FIG. 10 shows that the concentration of the glycated albumin and the hydrogen peroxide generated are correlated.

EXAMPLE 4

Determination of Glycation Rate of Human Serum Albumin

Glycated human serum albumin (Sigma Co.) (150 mg) and human serum albumin (Sigma Co.) (150 mg) were separately dissolved in 0.9% sodium chloride solution (3 ml). A series of solutions of different glycation rate were prepared by combining the previously prepared solutions. The glycation rate of the resultant solutions, when assayed using an automatic glycoalbumin measuring device (Kyoto Daichi Kagaku Co. Ltd.), was between 24.6 and 61.1%. The determination was carried out as follows.

1) Protease Treatment

A mixture of a glycated albumin solution (60 μl) and 12.5 mg/ml protease XIV (Sigma) solution (60 μl) was incubated at 37° C. for 30 minutes. The mixture was then heated at about 90° C. for 5 minutes to stop the reaction.

2) Determination of Activity

An FAOD reaction mixture was prepared by mixing 45 mM 4-aminoantipyrine solution (30 μl), 60 mM N-ethyl-N-(2-hydroxy-3-sulfopropyl)-m-toluidine solution (30 μl), peroxidase solution (60 units/ml) (30 μl), 0.1 M Tris-HCl buffer (pH 8.0) (300 μl), and FAOD-L solution (6 units/ml) (50 μl), and adjusting the total volume to 1 ml with distilled water. The FAOD-L solution (6 units/ml) was prepared by diluting the purified FAOD-L obtained in Example 2 with 0.1 M Tris-HCl buffer (pH 8.0).

Figure 11:
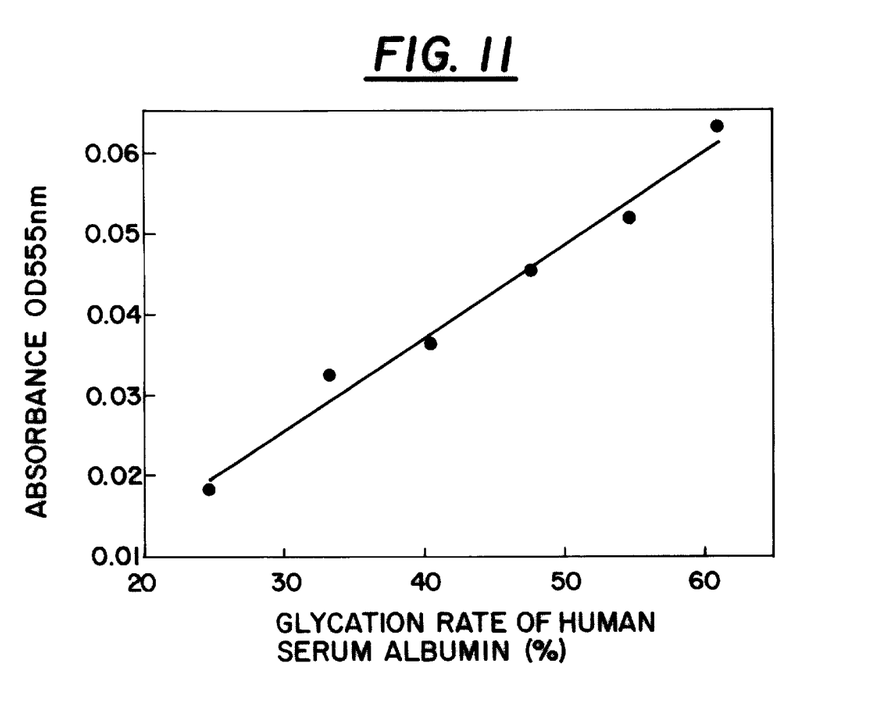
FIG. 11 is a graph illustrating the relation between the glycation rate of human serum albumin and the amount of hydrogen peroxide produced by the action of an FAOD-L.

After incubating the FAOD reaction mixture at 30° C. for 2 minutes, each of the protease-treated solution (100 μl) was added thereto. Thirty minutes later, the absorbance at 555 nm was measured. The relationships between the glycation rate of albumin and the absorbance are shown in FIG. 11, wherein the ordinate indicates the absorbance at 555 nm, which corresponds to the amount of hydrogen peroxide generated, and the abscissa the glycation rate of albumin. FIG. 11 shows that the glycation rate of albumin and the hydrogen peroxide generated are correlated.

EXAMPLE 5

Determination of Glycated Hemoglobin Level

A series of glycated hemoglobin solutions of different concentrations between 0 and 30% were prepared by dissolving glycohemoglobin control (Sigma) in distilled water. The determination was carried out using these solutions in a following manner.

1) Protease Treatment

A mixture of a glycated hemoglobin solution (25 μl), 500 units/ml aminopeptidase solution (5 μl) and 0.1 M Tris-HCl buffer (pH 8.0) was incubated at 30° C. for 30 minutes. To the mixture was added 10% trichloroacetic acid (50 μl) and stirred. After allowing to stand for 30 minutes at 0° C., the mixture was centrifuged at 12000 rpm for 10 minutes. The supernatant was neutralized with about 50 μl of 2M NaOH.

2) Determination of Activity

Figure 12:
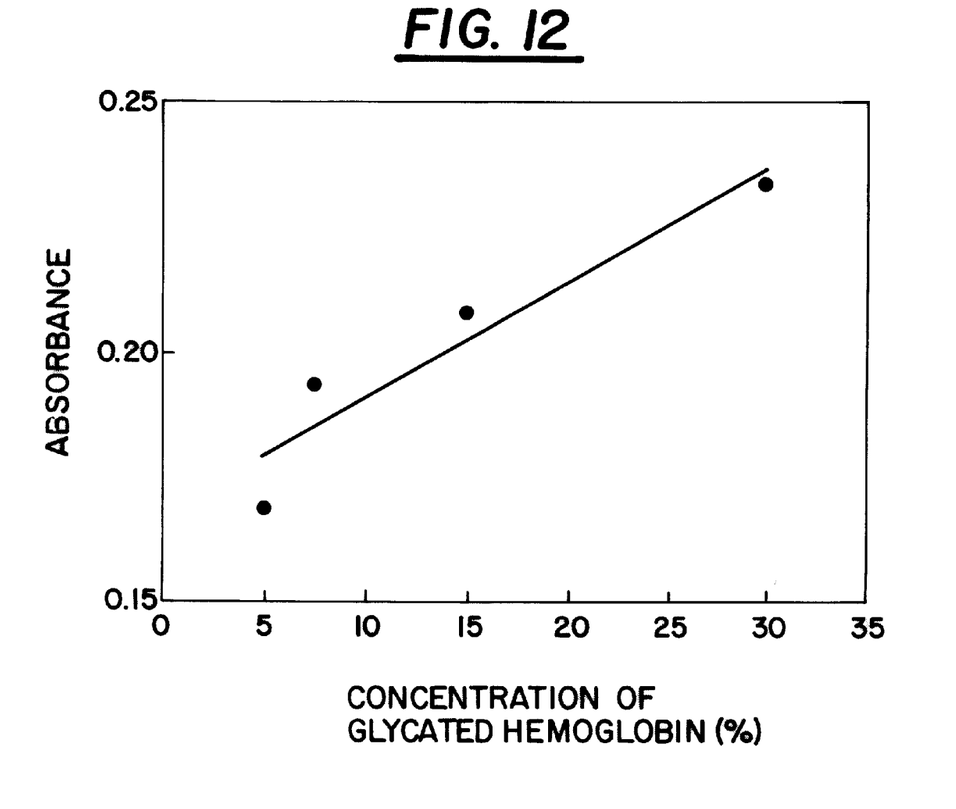
FIG. 12 is a graph illustrating a relation between the concentration of glycated hemoglobin and the amount of hydrogen peroxide produced by the action of an FAOD-L.

An FAOD reaction mixture was prepared by mixing 3 mM N-(carboxymethylaminocarbonyl)-4,4-bis (dimethylamino)biphenylamine solution (30 μl), peroxidase solution (60 units/ml) (30 μl), 0.1 M Tris-HCl buffer (pH 8.0) (300 μl) and FAOD-L solution (4 units/ml) (10 1), and adjusting the total volume to 1 ml with distilled water. The FAOD-L solution (4 units/ml) was prepared by diluting the purified FAOD-L obtained in Example 2 with 0.1 M Tri-HCl buffer (pH 8.0). After incubating the FAOD reaction mixture at 30° C. for 2 minutes, each of protease-treated solution (80 μl) was added thereto. Thirty minutes later, the absorbance at 727 nm was measured. The relationships between the concentration of glycated hemoglobin and the absorbance are shown in FIG. 12, wherein the ordinate indicates the absorbance at 727 nm, which corresponds to the amount of hydrogen peroxide generated, and the abscissa the concentration of glycated hemoglobin. FIG. 12 shows that the concentration of the glycated hemoglobin and the amount of hydrogen peroxide are correlated.

Industrial Utility

The FAOD of the present invention is distinct from conventional fructosyl amino acid oxidases in that it is specific to both of fructosyl lysine and fructosyl valine, and is more active on the former. Accordingly, it can be useful in the development of a novel clinical assay and food analysis, thereby greatly contributing to the improvement of diagnosis of diabetes and the quality control of food products. It is expected to be especially useful in the diagnosis of diabetes using as an index the concentration of glycated protein and/or glycation rate or the fructosamine level in blood. Also the reagent and assay involving the FAOD of the present invention render the determination of glycated protein highly accurate, thereby contributing to the diagnosis and control of diabetes.

What is claimed is:

1. A fructosyl amino acid oxidase from a culture of a strain of the genus Aspergillus, which has the following physico-chemical characteristics:

a) it catalyzes oxidation of an amadori campound in the presence of oxygen to generate α-ketoaldehyde, amine derivative and hydrogen peroxide;

b) it is active on fructosyl lysine and fructosyl valine as a substrate, wherein the substrate specificity on fructosyl lysine is higher than on fructosyl valine;

c) the optimum pH thereof is 8.5; and d) it is inhibited by manganese, cobalt, zinc or mercury ion.

2. A fructosyl amino acid oxidase from a culture of a strain of the genus Aspergillus, which has the following physico-chemical characteristics:

a) it catalyzes oxidation of an amadori campound in the presence of oxygen to generate α-ketoaldehyde, amine derivative and hydrogen peroxide;

b) it is active on fructosyl lysine and fructosyl valine as a substrate, wherein the substrate specificity on fructosyl lysine is higher than on fructosyl valine;

c) the molecular weight thereof is, when determined by gel filtration on Superdex 200 pg, about 94 kD; and d) it is inhibited by copper, zinc, silver or mercury ion.

3. The fructosyl amino acid oxidase of claim 1 or 2, wherein the strain of the genus Aspergillus is selected from the group consisting of *Aspergillus terreus* (IFO 6365, FERM BP-5756), *Aspergillus terreus* GP1 (FERM BP-5684), *Aspergillus oryzae* (IFO 4242, FERM BP-5757) and *Aspergillus oryzae* (IFO 5710).

4. A process for producing the fructosyl amino acid of claim 1 or 2 which comprises culturing a strain of the genus Aspergillus which produces a fructosyl amino acid oxidase in a medium comprising fructosyl lysine or fructosyl-$N^\alpha$-Z-lysine and recovering the fructosyl amino acid oxidase from the cultured medium.

5. The according to claim 4, wherein the strain of the genus Aspergillus is selected from the group consisting of *Aspergillus terreus* (IFO 6365, FERM BP-5756), *Aspergillus terreus* GP1 (FERM BP-5684), *Aspergillus oryzae* (IFO 4242, FERM BP-5757) and *Aspergillus oryzae* (IFO 5710).

* * * * *